United States Patent [19]

Tabaqchali et al.

[11] Patent Number: 5,459,034
[45] Date of Patent: Oct. 17, 1995

[54] DIFFICILE SPECIFIC OLIGONUCLEOTIDES

[75] Inventors: Soad Tabaqchali, London; Christopher L. Clayton; Brendan W. Wren, both of Hertfordshire, all of England

[73] Assignee: 3i Research Exploitation Limited, London, England

[21] Appl. No.: 849,438

[22] PCT Filed: Dec. 28, 1990

[86] PCT No.: PCT/GB90/02031

§ 371 Date: May 19, 1992

§ 102(e) Date: May 19, 1992

[87] PCT Pub. No.: WO91/09973

PCT Pub. Date: Jul. 11, 1991

[30] Foreign Application Priority Data

Dec. 29, 1989 [GB] United Kingdom ............ 8929293

[51] Int. Cl.$^6$ ............ C12Q 1/68; C07H 21/00; C12P 19/34
[52] U.S. Cl. ............ 435/6; 536/24.3; 536/24.33; 435/91.2
[58] Field of Search ............ 435/6, 91.2, 822; 536/24.3, 24.33; 935/77, 78

[56] References Cited

U.S. PATENT DOCUMENTS 4,965,188 10/1990 Mullis et al. ............ 435/6

FOREIGN PATENT DOCUMENTS 0153519 9/1985 European Pat. Off..
0154064 9/1985 European Pat. Off..

OTHER PUBLICATIONS

Price et al., Curr. Microbiol. 16(1):55–60 (1987) "Cloning of the carbohydrate–binding portion . . . ".
Eichel–Streiber et al., J. Gen. Microbiol. 135(1):55–64 (1989) "Cloning and Characterization of Overlapping . . . ".
Kim et al., J. Clin. Microbiol. 27(6):1192–1196 (1989) "Etiology of Childhood Diarrhea in Korea".
Muldrow et al., FEB 213(2):249–253 (1987) "Molecular cloning of *Clostridium Difficile* . . . ".
Figueiredo et al., Biochem. Soc. Trans. 14(3):640 (1986) "Luminescent detection system for non–radioactively . . . ".
Wren et al., FEBS Letters, 225:82–86 (1987) "Molecular cloning and expression . . . ".
J. of Clinical Microbiology, Sep. 1986, pp. 384–387 vol. 24 No. 3 Heard et al. "Immunoblotting to Demonstrate Antigenic and . . . difficile ".
J. Clinical Microbiology Dec. 1988, pp. 2484–2488, vol. 26, No. 12 Wilson et al. "Species–Specific Oligonucleotide Probes for rNA of . . . Species".
J. Clinical Microbiology Aug. 1990 pp. 1808–1812 vol. 28, No. 8 Wren et al. "Identification of Toxigenic Clostridium difficile Strains . . . Probe".
J. Clinical Microbiology Jan. 1991 pp. 33–37, vol. 29, No. 1 Kato et al. "Identification of Toxigenic Clostridum difficule . . . Reaction".
FEBS Letters 04525 vol. 213, No. 2, pp. 249–253 Muldrow et al. "Molecular cloning of Clostridium difficile toxin A gene . . . ".
Dialog Information Service, File 5: Biosis Previews 69–91/Mar. Biosis acc. no. 35037370 Diag Ass. No. 6171849 Fasching et al. "Oligonucleotide hybridization probe for detection of toxin A . . . ".

*Primary Examiner*—Margaret Parr
*Assistant Examiner*—Eggerton Campbell
*Attorney, Agent, or Firm*—Nixon & Vanderhye

[57] ABSTRACT

Oligonucleotides having substantially specific binding affinity towards *C. difficile* DNA are disclosed, especially oligonucleotides specific to the *C. difficile* A-toxin gene. Such oligonucleotides are useful as DNA probes and PCR primers in the detection of *C. difficile* in human clinical samples, e.g. fecal samples.

29 Claims, 1 Drawing Sheet

DIFFICILE SPECIFIC OLIGONUCLEOTIDES

This invention relates to oligonucleotides specific to bacteria of the species *Clostridium difficile* and useful as *C. difficile* DNA probes or in the amplification of *C. difficile* DNA.

*Clostridium difficile*, a Gram positive anaerobic spore-forming organism, is recognized as the major cause of pseudomembranous colitis and is implicated in antibiotic-associated colitis and diarrhoea. The pathogenicity of the organism is related to the production of an enterotoxin, toxin A, and a potent cytotoxin, toxin B. The diagnosis of *C. difficile*-associated disease depends on the isolation and identification of the organism and/or the demonstration of toxins in faecal specimens of patients and mono-specific antibodies for that purpose are disclosed in EP-A-0153519 and EP-A-0154064. Such procedures are time consuming, and a more rapid diagnosis is essential to enable the initiation of prompt therapy.

The present invention aims to avoid these difficulties by providing oligonucleotides specific to *C. difficile* DNA and is a development of the work reported in J. Clin. Microbiol. 24, 3, pp 384– 387 (Sep. 1986). In that paper, the results of immunoblot studies on various strains of *C. difficile* were reported to various immunogenic proteins were identified common to all nine *C. difficile* strains tested. In particular, three common antigens were potentially identified with molecular weights in the range 50 to 70 kDa.

Following on from those studies, further antigens have now been identified common to all *C. difficile* strains tested, and the genes encoding those antigens have been identified, cloned and, in one case, sequenced giving rise to the present invention, namely the construction, for the first time, of DNA probes and oligonucleotide primers specific to *C. difficile* DNA.

More specifically, in accordance with a first aspect of the present invention a 1947 bp DNA fragment encoding part of the A toxin gene of *C. difficile* has been identified, cloned and sequenced, the sequence being as set out in the Appendix I hereto as SEQ ID No.1 and which is to be taken as forming part of the present specification.

Analyzing that 1947 bp sequence in more detail, a continuous open reading frame is found containing four distinct groups of repeat nucleotide sequence with 88 to 100% identity within each group. These groups, identified herein as A, B, C, D (A=81 bp; B, C, D=63 bp) appear in the following arrangement:

ABCCCDABCDDABCCCDABCCDABCDABC where

A =
| 5' | ATA | GGG | GTG | TTT | AAA | GGA | CCT | AAA | GGA | TTT | GAA | TAT | TTT | GCA | |
| | Ile | Gly | Val | Phe | Lys | Gly | Pro | Lys | Gly | Phe | Glu | Tyr | Phe | Ala | |
| | CCT | GCT | AAT | ACT | TAT | AAT | AAT | AAC | ATA | GAA | GGT | CAG | GCT 3' | | nucleotides 1–81 of Seq. I.D. No. 1 |
| | Pro | Ala | Asn | Thr | Tyr | Asn | Asn | Asn | Ile | Glu | Gly | Gln | Ala | | |

B =
| 5' | ATA | GTT | TAT | CAA | AGT | AAA | TTC | TTA | ACT | TTG | AAT | |
| | Ile | Val | Tyr | Gln | Ser | Lys | Phe | Leu | Thr | Leu | Asn | |
| | GGT | AAA | AAA | TAT | TAC | TTT | GAT | AAT | AAC | TCA | 3' | nucleotides 82–144 of Seq I.D. No. 1 |
| | Gly | Lys | Lys | Tyr | Tyr | Phe | Asp | Asn | Asn | Ser | | |

C =
| 5' | GAA | GCA | GCT | ACT | GGA | TGG | CAA | ACT | ATT | GAT | GGT | |
| | Glu | Ala | Ala | Tyr | Gly | Trp | Gln | Thr | Ile | Asp | Gly | |
| | AAA | AAA | TAT | TAC | TTT | AAT | ACT | AAC | ACT | GCT | 3' | nucleotides 208–270 of Seq I.D. No. 1 |
| | Lys | Lys | Tyr | Tyr | Phe | Asn | Tyr | Asn | Tyr | Ala | | | and

D =
| 5' | ATA | GCT | TCA | ACT | GGT | TAT | ACA | ATT | ATT | AAT | GGT | |
| | Ile | Ala | Ser | Thr | Gly | Tyr | Thr | Ile | Ile | Asn | Gly | |
| | AAA | CAT | TTT | TAT | TTT | AAT | ACT | GAT | GGT | ATT | 3' | nucleotides 334–396 of Seq I.D. No. 1 |
| | Lys | His | Phe | Tyr | Phe | Asn | Thr | Asp | Gly | Ile | | |

The repeating sequence of the A, B, C and D blocks given above account for 1935 bp of the 1947 bp fragment. The remaining 12 are accounted for two linking areas each of 6 bp which occur between the A and D groups underlined.

Utilizing that information oligonucleotides and DNA probes capable of hybridizing to the *C. difficile* A toxin gene and potentially useful in the early detection of *C. difficile* infection may now be constructed. The probes may range in size from virtually the complete 1947 nucleotide sequence given in the appendix hereto, SEQ ID No 1 down to sequences of a more appropriate length for oligonucleotide synthesis, for example, sequence of from 15 to 300 nucleotides, more usually of from 15 to 50 nucleotides and especially from 15 to 30. The final selection of a particular oligonucleotide, or pair of oligonucleotides will depend upon a number of factors, well understood in the art, and including amongst others the stringency requirements, i.e. the ability or otherwise of the probe to tolerate local mismatching with the complementary sequence in the target DNA. Obviously the longer the probe the better the ability to withstand local mismatching without adversely affecting the hybridization of the oligonucleotide to the target DNA. However, the length of the oligonucleotide always has to be balanced against other factors such as ease of synthesis. The factors affecting that choice are, however, well recognized and well within the capabilities of the person skilled in the art.

Also, as the person skilled in the art will recognize, references herein to particular oligonucleotides and sequences in single stranded form and including the complete 1947 bp sequence, and which are written, as is required, reading from left to right, i.e. from the 5' terminus to the 3' terminus, automatically include the complementary sequence. Not only that, but oligonucleotide sequences given herein as DNA sequences can equally well be constructed as RNA sequences with uracil (U) replacing thymine (T).

Whilst, as indicated, the generality of the present invention extends to DNA (and RNA) probes complementary to any sequence of nucleotide bases to be found in the 1947 bp sequence set out hereinafter, certain sequences and pairs of sequences can be identified as being particularly preferred. For example, sequences selected from the repeat sequences already given are especially preferred as being complementary to two spaced but identical sections of the *C. difficile* A toxin gene. One such sequence is the 25 unit oligonucleotide:

| BW71: | |
|---|---|
| 5' AAACTATTGA TGGTAAAAAA TATTA 3' | nucleotides 227–251 of Seq I.D. No. 1 |

(BW71 is simply an identification code) which sequence is to be found in the Toxin A Repeat C sequence given above.

A more particular aspect of the present invention relates to selected pairs of *C. difficile* oligonucleotide probes which can be used to amplify the *C. difficile* A toxin gene or sections thereof by polymerase chain reaction (PCR) technology and using selected pairs of oligonucleotides as primers.

In recent years PCR has developed into a major tool in DNA probe technology enabling highly sensitive detection of minute amounts of genetic material present in a sample by first amplifying the gene or gene fragment by PCR to replicate a multiplicity of identical gene or gene fragments. Not only does that enable better detection of that gene or gene fragment, but it provides a substantial reservoir of genetic material for subsequent research and analysis, and for subsequent cloning and expression in a suitable vector. However, PCR presupposes at least some knowledge of the nucleotide sequence in the gene or gene fragment to be amplified, in view of the need to provide an oligonucleotide primer for the PCR, which primer hybridized to the complementary sequence in the gene or gene fragment to be amplified and which initiates the PCR replication of the gene or gene fragment from that point. The use of a pair of primers which hybridize to the target DNA at different spaced apart locations enable precise lengths of the target gene or gene fragment to be amplified. Once again, it is theoretically possible to use any pair of oligonucleotides hybridizable at different points of the *C. difficile* A toxin gene as primers for the PCR amplification and subsequent detection of that gene, and consequently the detection of *C. difficile* in a sample, e.g. a clinical sample. However, it is preferable to use as primers for the PCR oligonucleotide which hybridize to spaced locations on one of the repeat sequences now identified as appearing in the *C. difficile* A toxin gene. Thus, in the amplification of the gene by PCR replication of the repeat sequence occurs in parallel at each location of that sequence in the gene, thus substantially increasing the replication rate, and increasing not only the sensitivity of the *C. difficile* detection, but also dramatically reducing that time required to carry out a diagnosis of *C. difficile* infection in a patient. In tests carried out by the present inventors, positive diagnoses of *C. difficile* infection have been confirmed by PCR within the space of five hours.

Based on the repeat sequences given above, various oligonucleotide pairings can be suggested of various different lengths and comprising a sequence of nucleotides complementary to the sequences at the 5'- and 3'- ends of each repeat sequence. Especially preferred are pairs of oligonucleotides complementary to the 5' and 3' termini of the tandem C repeat sequence. Two particular pairings which have been synthesized and used in accordance with this invention are

| BW69: | | | |
|---|---|---|---|
| 5' GAAGCAGCTA | CTGGATGGCA | 3' | nucleotides 208–227 of Seq I.D. No. 1. |
| BW70: | | | |
| 5' AGCAGTGTTA | GTATTAAAGT | 3' | complementary to nucleotides 251–270 of Seq I.D. No. 1 | complementary to the opposite ends of the *C. difficile* A toxin gene repeat sequence C, and

| BW65: | | | |
|---|---|---|---|
| 5' ATAGGGGTGT | TTAAAGGACC T 3' | | nucleotides 1–21 of Seq. I.D. No. 1. |
| BW66: | | | |
| 5' AGCCTGACCT | TCTATGTTAT 3' | | complementary to nucleotides 62–81 of Seq. I.D. No. 1 | complementary to the opposite ends of the *C. difficile* A toxin gene repeat sequence A.

In general terms, the preferential pairings for PCR amplification of the *C. difficile* A toxin gene fragments may be identified as oligonucleotide sequences of from 15–25 nucleotides complementary to the 15 to 25 nucleotide sequences at the 5' to 3' ends of the A, B, C and D repeat sequences identified above, and especially of the A and C sequences.

In accordance, with a second aspect of the present invention a 31 kDa antigen has been identified as common to all C. *difficile* strains tested, and has been found to be encoded by a 1.8 kb HindIII digestion fragment of C. *difficile* DNA. Thus, in accordance with a second aspect of the present invention, C. *difficile* probes are provided derived from or complementary to 1.8 kb HindIII digestion fragment of C. *difficile* or to individual sequences of that fragment and comprising oligonucleotides again ranging in size from 15 units to substantially the complete sequence, but more usually ranging in size from 15 to 300 units, most usually 15 to 50 units, more preferably 15 to 30 units.

Although the correct reading frame has yet to be established, the complete sequence of the 1.8 kb HindIII digestion fragment encoding the 31 kDa C. *difficile* antigen is as set out in Appendix II as SEQ ID No.2 and which again is to be taken as form a part of the present specification.

Particular oligonucleotide probes complementary to selected sequences of the 1.8 kb HindIII fragment are identified as follows, the numbers in parentheses are simply identification codes.

| Probe | | Hind III Fragment Sequence nt. numbers |
|---|---|---|
| (028) 5'AAAAATGCTC | AGCTTGCAG 3' | nucleotides 318–336 of Seq. I.D. No. 2 |
| (031) 5'AAAAATTTAA | CTAAGTT 3' | nucleotides 234–750 of Seq. I.D. No. 2 |
| (029) 5'AACAATTTTA | TTTAAAC 3' | complementary to nucleotides 1460–1476 of Seq. I.D. No. 2 |
| (032) 5'TTTTGATGTT | AACTGACC 3' | complementary to nucleotides 1058–1075 of Seq. I.D. No. 2 |
| (037) 5'GTTACTTTTG | ATACAGTA 3' | nucleotides 1076–1093 of Seq. I.D. No. 2 |

In a broad aspect therefore, the present invention provides C. *difficile* specific oligonucleotides comprising oligonucleotides of at least 15 nucleotides complementary to, and capable to hybridization with, any sequence of 15 or more nucleotide bases of the DNA sequences hereinbefore set forth and identified respectively as the 1.8 kb HindIII DNA fragment of C. *difficile* and the 1947 bp A Toxin DNA fragment, said probes having a length upto and including the complete sequence.

Within that broad class, two broad sub-categories can be identified as constituting or including the preferred C. *difficile* specific oligonucleotides according to this invention. The first sub-category is constituted by sub-restriction fragments of either complete sequence, and as such sub-restriction fragments there may be especially identified the following:

An Eco RI/PstI 1448 bp sub-restriction fragment of the Toxin A gene.

Such restriction fragments may, of course, be obtained in known manner, for example by digestion of C. *difficile* genomic DNA with the appropriate restriction enzyme or enzymes and subsequent separation by gel electrophoresis, chromatography or in any other suitable manner known for the separation of individual DNA restriction fragments according to size.

The second principal sub-category of DNA probes according to the invention are synthetic oligonucleotide sequences, e.g. those already mentioned. Such oligonucleotide sequences are readily assembled using known oligonucleotide synthesis techniques.

Utilising selected complementary pairs of the above oligonucleotides as primers, polymerase chain reactions (PCR) have been carried out according to manufacturers specifications (Cetus Ltd.) to amplify known fragments of C. *difficile* DNA, both purified total C. *difficile* DNA and crude C. *difficile* DNA released from C. *difficile* bacterial cells. In these experiments:

oligonucleotides 031 and 032 have been shown to amplify a 0.303 kb fragment of C. *difficile* DNA;

oligonucleotides 028 and 029 have been shown to amplify a 1.2 kb fragment of C. *difficile* DNA;

oligonucleotides 031 and 029 have been shown to amplify a 0.7 kb fragment of C. *difficile* DNA;

oligonucleotides 037 and 029 have been shown to amplify a 0.35 kb fragment;

oligonucleotides 029 and 032 have been shown to amplify a 0.8 kb fragment of C. *difficile* DNA; and Although PCR amplification appears to be the presently preferred method of C. *difficile* detection using the C. *difficile* specific oligonucleotides of this invention, other detection procedures are available and are well known in the art. To this end the C. *difficile* specific oligonucleotides of this invention may be provided with a variety of different labels: radioactive, fluorescent or enzyme, to provide a variety of DNA probes specific to C. *difficile* DNA and all permitting the detection of hybridized (bound) DNA probe to the unidentified DNA sample under investigation. Alternatively, of course, for sandwich hybridization techniques the DNA probes of this invention may be immobilized in any known appropriate fashion, e.g. by covalent bonding to a variety of different solid substrates, both particulate, e.g. glass, Sephadex, Sephacryl beads etc., and continuous surface substrates. The techniques of DNA labelling and immobilization are well known in the art, as are methods for the detection of microorganisms, in general, utilizing DNA probes and which will be equally suitable in accordance with the present invention for the specific detection of C. *difficile*. Such procedures and methods are not part of the present invention as such and need not be further described here.

However, it is to be understood that references herein to an oligonucleotide for use as DNA (or RNA) probe in accordance with this invention are to be taken as including also labelled, tailed and immobilized versions thereof as well as the oligonucleotide sequence per se, it also being understood that oligonucleotide lengths given herein do not include additional non-complementary sequences, such as poly(DA) or poly(DT) tails added for a specific purpose such as immobilizing the probe on a poly(DT) or poly(DA) coated surface.

The C. *difficile* specific oligonucleotides covered by this invention include both single- and double-stranded versions, it being understood that in any subsequent hybridization procedures such as the detection of C. *difficile* in clinical, faecal or other samples, such double-stranded oligonucleotide will require denaturing to provide the probes in single-stranded form.

Also included within the scope of this invention are a method of detecting the presence of C. *difficile* in a sample, for example a faecal sample, which comprises treating the sample to release the DNA or mRNA and detecting the presence of C. *difficile* DNA or mRNA using a C. *difficile* specific oligonucleotide according to the invention, and especially a pair of such oligonucleotides as primers for a PCR reaction and diagnostic kits for the diagnosis of *C. difficile* infection in a patient comprising a *C. difficile* specific oligonucleotide according to the invention, and especially PCR kits containing a pair of such oligonucleotides for use as primers in the PCR reaction.

The invention is illustrated by the following Examples:

EXAMPLE 1

PCR amplification of *C. difficile* A toxin gene using oligonucleotides BW69 and BW70

SAMPLE PREPARATION

Nine stranded *C. difficile* strains, labelled A to E and W to Z were grown anaerobically at 37° C. for 36 hours on selective media (cycloserine, cefoxitin and fructose sugar). Strains B, D, E, W, X and Z were specifically selected as being known to be toxigenic. Strains A, C and Y selected as controls were known to be non-toxigenic.

Single colonies of each strain were scraped with an inoculating loop into a 1.5 ml polypropylene tube containing 200 μl sterile water and boiled for 10 minutes. The samples were then centrifuged for 5 minutes at 14000×g to obtain a supernatent *C. difficile* cell extract.

OLIGONUCLEOTIDE POLYMER SYNTHESIS

Oligonucleotides BW69 and BW70 (see above) were synthesized on an Applied Biosystems synthesizer using the automated phosphoramidite coupling method.

PCR

Two microliters of each *C. difficile* extract were added to a 100 μl reaction volume with 10 mM tris-HCl (pH 8.3), 0.01% gelatin, 200 μM of each of the four deoxytribonucleotides: A, C, T, G, $100_D$M of each of the two primers and 250 Taq polymerase (Perkin-Elmer Cetus, Calif.). The reaction mixtures were overlain with paraffin oil (100 μl) placed in a thermal (Hybaid Ltd.) and amplified for 30 cycles. A rapid two step cycle of 94° C. and 46° C. for 30 seconds each was used except that the first 94° C. step was extended to 3 minutes to ensure denaturation of the initial sample.

PRODUCT SEPARATION

20 μl aliquots of the amplified samples were electrophoresed in a horizontal 4% Nusieve GTG agarose gel (ICN Biochemicals Ltd.) containing 0.5 μl ethidium bromide per ml, and the bands visualized under UV light.

In a parallel series of experiments, the cultured *C. difficile* strain W was serially diluted to provide samples containing 300, 30 and 3 bacteria (as well as $10^7$ other anaerobic enteric bacteria from the original faecal sample) which were likewise subjected to PCR with primers BW69 and BW70 (samples 1, 2 and 3).

RESULTS

Figure 1:
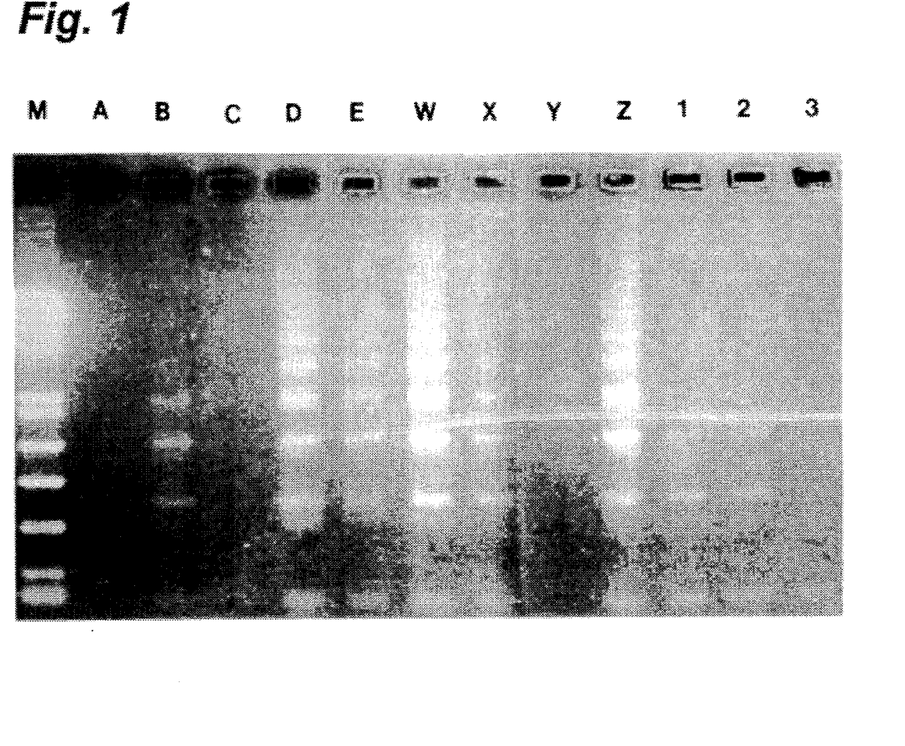
FIG. 1 is a photograph showing the bands obtained by subjecting genetic DNA from *C. difficile* to PCR amplification using oligonucleotides according to the present invention as primers and subjecting the product of the CR reaction to separation on an agarose gel.

The results are shown in FIG. 1 of the accompanying drawings which shows the band separation obtained with each of the samples A to E, W to Z and 1, 2 and 3. Lane M is that of a parallel DNA size marker giving bands at 67 80 110 147 190 242 and 267 bp.

Lanes B, D, E, W, X, Z, 1 and 2 (toxigenic *C. difficile* strains) each sow a characteristic five bands at 63 126 189 252 and 315 bp, which are not present in samples from the non-toxigenic strains (A, C and T), but which are apparent with samples containing as few as 300 or even 30 bacteria.

These results have been confirmed on a total of 45 *C. difficile* strains by PCR amplification using the primer pair BW69 and BW70. Of the 45 strains tasted, all 33 strains known to be toxigenic proved positive, whilst the 12 non-toxigenic strain proved negative.

Of 16 strains from 13 different species of Clostridium other than *C. difficile*, only three, all *C. sordelii*, have given positive results.

These results are tabulated in Table 1 and clearly show the substantial specificity of the present oligonucleotides towards toxigenic *C. difficile*, and the fact that positive diagnosis can be made on the basis of as few as 30 bacteria establishes its sensitivity. One of the reasons for this degree of sensitivity is conjectured to be the specific selection of a pair of primers complementary to the 5' and 3' ends of the *C. difficile* A toxin gene repeat sequence C. Virtually equivalent results can, however, be predicted for similar pairs of primers complementary to the 5' and 3' ends of the repeat sequences A, B and D.

EXAMPLE 2

PCR amplification of *C. difficile* DNA using oligonucleotide probes 028 and 029

Oligonucleotides 028 and 029 were synthesised as before on an Applied Siosystems synthesiser.

The two primers were then used at a concentration of 1 μM to amplify *C. difficile* DNA obtained by boiling *C. difficile* cells in 50 μl of $H_2O$ for 10 minutes. The DNA was amplified using a cycle profile of 94° C. 1 min., 31° C. 1 min., and 72° C. 3 min. After the last cycle the polymerization step was extended from 3 to 10 minutes. Twenty six cycles of amplification were performed in total. The reactions were carried out in 100 μl volumes, 20 μl samples were run on agarose gels and amplified DNA detected by ethidium bromide staining and comparison with mol. wt. standards. By this method *C. difficile* DNA has been amplified from cell population as low as $10^2$ *C. difficile* cells, thus indicating the extreme sensitivity of *C. difficile* specific oligonucleotides according to this invention. Simultaneous controls with other Clostridia spp. have failed to produce any evidence of amplification, indicating the specificity of probes according to the present invention to *C. difficile*.

Confirmation that the amplified fragments are *C. difficile* DNA is obtained both by hybridization with internal oligonucleotide probes and by using two internal primers for PCR after initial amplification, e.g. by using probes 028 and 029, to give amplified fragments of 1.2 kb, and then using 2% of this reaction product to perform further PCR with probes 037 and 029 to give a 0.35 kb fragment.

EXAMPLE 3

PCR amplification of *C. difficile* DNA using primers BW65 and BW66.

Following the same protocol as in Example 1, DNA was amplified from toxigenic and non-toxigenic *C. difficile* strains using primers BW65 and BW66.

Figure 2:
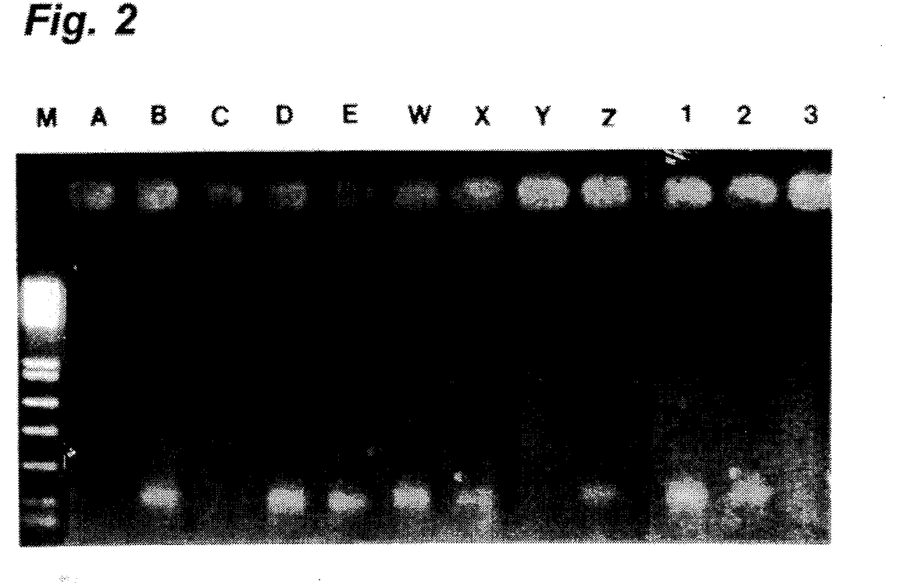
FIG. 2 is a similar photograph but showing the results obtained using a different pair of primers for the PCR reaction.

The results are shown in FIG. 2. Lanes B D E W X and Z show the PCR amplified products from pure colonies of toxigenic *C. difficile* and Lanes A C and Y the non-toxigenic strains. Lanes 1, 2 and 3 serial dilutions of G toxigenic *C. difficile* strain W at 300 30 and 3 bacteria mixed with $10^7$ other anaerobic enteric bacteria. Lane M is a molecular weight size marker showing DNA lanes at 67 80 110 147

190 242 and 267 bp. (BshI and MspI digests of plasmid pHC 314).

The results obtained in Examples 1 and 3 are summarized in Table 1 below.

TABLE 1

Summary of PCR experiments with various clostridial strains using either pair of primers BW 65/66 or BW 69/70.

|  | No. tested | PCR positive | PCR negative |
|---|---|---|---|
| Toxigenic C. difficile | 33 | 33 | 0 |
| Non-Toxigenic C. difficile | 12 | 0 | 12 |
| Other Clostridial species | 16 | 3 | 13 |

These results clearly establish the specifity and sensitivity of the preferred oligonucleotides of the present invention i.e. those complementary to the terminal sequences of the A and C A-toxin repeat sequences, and indicate their utility as a tool in the detection and diagnosis of infections by *C. difficile*.

APPENDIX 1.

SEQ ID No.1
Sequence Type: Nucleotide
Sequence Length: 1947 bp
Strandedness: Double
Topology: Linear
Molecule Type: Genomic DNA
Original Source: *C. difficile*
Immediate: Bacteriophage λEMBL3 *C. difficile*
Experimental Source: gene library screening and subcloning into *E. coli*
Features: Not yet fully established.
Properties: *C. difficile* A Toxin gene (fragment)

5' ATAGGGGTGTTTAAAGACCTAAAGGATTTGAATATTTTGCACCTGCTAATACTTATAATAATAACATAGAAGGT
CAGGCTATAGTTTATCAAAGTAAATTCTTAACTTTGAATGGTAAAAAATATTACTTTGATAATAACTCAAAAGCA
GTTACCGGATGGCAAACTATTGATAGTAAAAAATATTACTTTAATACTAACACTGCTGAAGCAGCTACTGGATGG
CAAACTATTGATGGTAAAAAATATTACTTTAATACTAACACTGCTGAAGCAGCTACTGGATGGCAAACTATTGAT
GGTAAAAAATATTACTTTAATACTAACACTGCTATAGCTTCAACTGGTTATACAATTATTAATGGTAAACATTTT
TATTTTAATACTGATGGTATTATGCAGATAGGAGTGTTTAAAGGACCTAATGGATTTGAATATTTTGCACCTGCT
AATACGGATGCTAACAACATAGAAGGTCAAGCTATACTTTACCAAAGTGAATTCTTAACTTTGAATGGTAAAAAA
TATTATTTTGATAATAACTCAAAAGCAGTTACCGGATGGCAAACTATTGATAGTAAAAAATATTACTTTAATACT
AACACTGCTATAGCTTCAACTGGTTATACTATTATTAATGGAAAACATTTTTATTTAAATACTGATGGTATTATA
GCTTCAACTGGTTATACAATTATTAATGGTAACCATTTTTATTTTAATACTGATGGTATTATGAAAATAGGGGTT
TTTAAAGGACCTAATGGATTTGAATATTTTGCACCTGCTAATACTGATCATAATAATAGAAGGTCAGGCTATA
GTTTATCAAAGTAAATTCTTAACTTTGAATGGTAAAAAATATTATTTTGATAATAATTCAAAAGCAGTTACTGGA
TGGCAAACTATTGATAGTAAAAAATATTACTTTAATACTAACACTGCTGAAGCAGCTACTGGATGGCAAACTATT
GATGGTAAAAAATATTACTTTAATACTAACACTGCTGAAGCAGCTACTGGATGGCAAACTATTGATGGTAAAAA
ATATTACTTTAATACTAACACTGCTATAGCTTCAACTGGTTATACAATTATTAATGGTAAACATTTTTATTTTAAT
ACTGATGGTATTATCGGAGTGTTTAAAGGACCTAATGGATTTGAATATTTTGCACCTGCTAATACTGATGCTAAT
AACATAGAAGGTCAAGCTATAGTTTATCAAAGTAAATTTTTAACTTTGAATGGTAAAAAATATTACTTTGATAAT
AACTCAAAAGCAGTTACTGGATGGCATACTATTGATAGTAAAAAATATTACTTTAATACTAACACTGCTGAAGCA
GCTACTGGATGGCAAACTATTGATGGTAAAAAATATTACTTTAATACTAACACTGCTATAGCTTCAACTGGTTAT
ACAATTAATAATGGAAAACATTTTTATTTTAATACTGATGGTATTATAGGAGTGTTTAAAGGACCTAATGGATTT
GAATATTTTGCACCTGCTAATACGGATGCTAACAACATAGAAGGTCAAGCTATAGTTTATCAAAGTAAATTCTTA
ACTTTGAATGGTAAAAAATATTATTTTGATAATAACTCAAATGCTGTTACCGGATGTCAAACTATTGATAGTAAA
AAATATTACTTTAATACTAACACTGCTATAGCTTCAACTGGTTATACAATTATTAATGGTAAACATTTTTATTTT
AATACTGATGGTATTATAGGGGTGTTTAAAGGTCCTAATGGATTTGAATATTTTGCACCTGCTAATACTTATGAT
AATAACATAGAAGGTCAGGCTATAGTTTATCAAAGTAAATTATTAACTTTGAATGGTAAAAAATATTATTTTGAT
AATAACTCAAAAGCAGTTACCGGATGGCAAACTATTGATAGTAAAAAATATTACTTTAATACTAACACTGCAG 3'

APPENDIX II.

SEQ ID No.2
Sequence Type: Nucleotide
Sequence Length: 1853 bp
Strandedness: Double
Topology: Linear
Molecule type: Genomic DNA
Original source: *C. difficile*
Immediate experimental source: *C. difficile* by Hind III digestion
Features: Not yet established.
Properties: Not known.

| | | | | | | | |
|---|---|---|---|---|---|---|---|
| AAAATAGTAA | AAAAGTAGTG | ATAGCTGCTG | TAAACGGATT | TGCTTTAGGT | GGATGTGAAC | 60 |
| TTGCAATGGC | ATGTGATATA | AGAATTGCAT | CTGCTAAAGC | TAAATTTGGT | CAGCCAGAAG | 120 |
| TAACTCTTGG | AATAACTCCA | GGATATGGAG | GAACTCAAAG | GCTTACAAGA | TTGGTTGGAA | 180 |
| TGGCAAAAGC | AAAACAATTA | ATCTTTACAG | GTCAAGTTAT | AAAAGCTGAT | GAAGCTGAAA | 240 |
| AAATAGGGCT | AGTAAATAGA | GTCGTTGAGC | CAGACATTTT | AATAGAAGAA | GTTGAGAAAT | 300 |
| TAGCTAAGAT | AATAGCTAAA | AATGCTCAGC | TTGCAGTTAC | ATACTCTAAA | GAAGCAATAC | 360 |
| ACTTGGTGCT | CAAACTGATA | TAAATACTGG | AATAGATATA | GAATCTAATT | TATTTGGTCT | 420 |
| TTGTTTTTCA | ACTAAACACC | AAAAAGAAGG | AATGTCAGCT | TTCGTTGAAA | AGAGAGAAGC | 480 |
| TAAGTTTATA | AAAGGGTAAA | AATCTAATTA | AAAATATATT | TGCTGTTAAC | TAGAATAATT | 540 |
| TAAATAGTAT | TTTAATCTAG | TTAACATAAT | ATAAATACTA | AAATAACAGG | AGGTTATAAC | 600 |
| TATGAAATTA | GCTGTAATAG | GTAGTGGAAC | TATGGGAAGT | GGTATTGTAC | AAACTTTTGC | 660 |
| AAGTTGTGGA | CATGATGTAT | GTTTAAAGAG | TAGAACTCAA | GGTGCTATAG | ATAAATGTTT | 720 |
| AGCTTTATTA | GATAAAAATT | TAACTAAGTT | AGTTACTAAG | GGAAAATGGA | TGAAAGCTAC | 780 |
| AAAAGCAGAA | ATATTAAGTC | ATGTTAGTTC | AACTACTAAC | TATGAAGATT | TAAAAGATAT | 840 |
| GGATTTAATA | ATAGAAGCAT | CTGTAGAAGA | CATGAATATA | AAGAAAGATG | TTTTCAACTT | 900 |
| ACTAGATGAA | TTATGTAAAG | AAGATACTAT | CTTGGCAACA | AATACTTCAT | CATTATCTAT | 960 |
| AACAGAAATA | GCTTCTTCTA | CTAAGAGACC | AGATAAAGTT | ATAGGAATGC | ATTTCTTTAA | 1020 |
| TCCAGTTCCT | ATGATGAAAT | TAGTTGAAGT | TATAAGTGGT | CAGTTAACAT | CAAAAGTTAC | 1080 |
| TTTTGATACA | GTATTTGAAT | TACTTAAGAG | TATCAATAAA | GTACCAGTAG | ATGTATCTGA | 1140 |
| ATCTCCTGGA | TTTGTAGTAA | ATAGAATACT | TATACCTATG | ATAAATGAAG | CTGTTGGTAT | 1200 |
| ATATGCAGAT | GGTGTTGCAA | GTAAAGAAGA | AATAGATGAA | GCTATGAAAT | TAGGAGCAAA | 1260 |
| CCATCAATGG | ACCACTAGCA | TTAGGTGATT | TAATTGGATT | AGATGTTGTT | TTAGCTATAA | 1320 |
| TGAACGTTTT | ATATACTGAG | TTTGGAGATA | CTAAATATAG | ACCTCATCAC | TTTTAGCTAA | 1380 |
| AATGGTTAGA | GCTAAGCAAT | TAGGAAGAAA | AACTAAGATA | GGATTCTATG | ATTATAATAA | 1440 |
| ATAAGAATTT | GGAATAAAAG | TTTAAATAAA | ATTGTTTAAA | AACAATTTCG | ATATATGAAA | 1500 |
| AAATCTAATT | TAATGGGGGT | AATGATATGA | GAGAAGTAGT | AATTGCCAGT | GCAGCTAGAA | 1560 |
| CAGCAGTAGG | AAGTTTTGGA | GGAGCATTTA | AATCAGTTTC | AGCGGTAGAG | TTAGGGGTAA | 1620 |
| CAGCAGCTAA | AGAAGCTATA | AAAAGAGCTA | ACATAACTCC | AGATATGATA | GATGAATCTC | 1680 |
| TTTTTAGGGG | GAGTACTTAC | AGCAGGTCTT | GGACAAAATA | TATAGCAAGA | CAAATAGCAT | 1740 |
| TAGGAGCAGG | AATACCAGTA | GAAAAACCAG | CTATGACTAT | AAATATACTT | TGTGGTTCTG | 1800 |
| GATTAAGATC | GTGGCGGGCA | CTCCGAACGT | GAACGGGTCC | GCGTCGACCT | GCA | 1853 |

We claim:

1. An oligonucleotide for use in detecting DNA or RNA from microorganisms of the species *Clostridium difficile*, said oligonucleotide being selected from the group consisting of the sequences:

| | | | |
|---|---|---|---|
| i) | A | 5' ATAGGGGTGT TTAAAGGACC TAAAGGATTT GAATATTTTG CACCTGCTAA TACTTATAAT AATAACATAG AAGGTCAGGC T 3' | nucleotides 1-81 of Seq. I.D. No. 1. |
| ii) | B | 5' ATAGTTTATC AAAGTAAATT CTTAACTTTG AATGGTAAAA AATATTACTT TGATAATAAC TCA 3' | nucleotides 82-144 of Seq. I.D. No. 1. |
| iii) | C | 5' GAAGCAGCTA CTGGATGGCA AACTATTGAT GGTAAAAAAT ATTACTTTAA TACTAACACT GCT 3' | nucleotides 208-270 of Seq. I.D. No. 1. |
| iv) | D | 5' ATAGCTTCAA CTGGTTATAC AATTATTAAT GGTAAACATT TTTATTTTAA TACTGATGGT ATT 3' | nucleotides 334-396 of Seq. I.D. No. 1. | v) DNA sequences consisting of sequences that are fully complementary to sequence A, B, C or D;
vi) DNA sequences that are partial subsequences of the DNA sequence A, B, C or D, such partial subsequences having a minimum of 15 consecutive nucleotide bases;
vii) DNA sequences that are partial subsequences of the DNA sequences that are fully complementary to sequence A, B, C or D, such partial subsequences having a minimum of 15 consecutive nucleotide bases;
viii) RNA sequences having a sequence as defined in sequence A, B, C or D, but with U replacing T; and
ix) RNA sequences having a partial subsequence of sequence A, B, C or D, the partial subsequence having a minimum of 15 consecutive nucleotide bases and with U replacing T in the partial sequence.

2. An oligonucleotide according to claim 1, wherein said oligonucleotide is from 15 to 30 nucleotide bases in length.

3. An oligonucleotide for use in detecting DNA or RNA from microorganisms of the species *Clostridium difficile*, said oligonucleotide being selected from the group consisting of:

| | | | |
|---|---|---|---|
| i) | A | 5' ATAGGGGTGT TTAAAGGACC TAAAGGATTT GAATATTTTG CACCTGCTAA TACTTATAAT AATAACATAG AAGGTCAGGC T 3' | nucleotides 1-81 of Seq. I.D. No. 1 |
| ii) | C | 5' GAAGCAGCTA CTGGATGGCA AACTATTGAT GGTAAAAAAT ATTACTTTAA TACTAACACT GCT 3' | nucleotides 208-270 of Seq. I.D. No. 1 | iii) DNA sequences consisting of sequences that are fully complementary to sequence A and C;
iv) DNA sequences that are partial subsequences of the DNA sequence A or C, such partial subsequences having a minimum of 15 consecutive nucleotide bases;
v) DNA sequences that are partial subsequences of the DNA sequences that are fully complementary to sequence A or C, such partial subsequences having a minimum of 15 consecutive nucleotide bases;
vi) RNA sequences having a sequence as defined in sequence A or C but with U replacing T; and
vii) RNA sequences having a partial subsequences of A or C, the partial subsequence having a minimum of 15 consecutive nucleotide bases and with U replacing T in the partial sequence.

4. An oligonucleotide according to claim 3, wherein said oligonucleotide is from 15 to 30 nucleotide bases in length.

5. The oligonucleotide
5' GAAGCAGCTA CTGGATGGCA 3' nucleotides 208–226 of Seq. I.D. No.1.

6. The oligonucleotide
5' AGCAGTGTTA GTATTAAAGT 3' complementary to nucleotides 251–270 of Seq. I.D. No.1.

7. The oligonucleotide
5' ATAGGGGTGT TTAAAGGACC T 3' nucleotides 1.21 of Seq. I.D. No.1.

8. The oligonucleotide
5' AGCCTGACCT TCTATGTTAT 3' complementary to nucleotides 62–81 of Seq. I.D. No.1.

9. An oligonucleotide according to claim 1, wherein said oligonucleotide is a DNA sequence.

10. An oligonucleotide according to claim 3, wherein said oligonucleotide is a DNA sequence.

11. An oligonucleotide probe for use in detecting DNA or RNA from microorganisms of the species *Clostridium difficile*, said probe consisting of an oligonucleotide sequence labelled with a label permitting detection of the probe when hybridized to a complementary sequence of *C. difficile* DNA or mRNA, said oligonucleotide sequence being selected from the group consisting of

| | | | |
|---|---|---|---|
| i) | A | 5' ATAGGGGTGT TTAAAGGACC TAAAGGATTT GAATATTTTG CACCTGCTAA TACTTATAAT AATAACATAG AAGGTCAGGC T 3' | nucleotides 1-81 of Seq. I.D. No. 1. |
| ii) | B | 5' ATAGTTTATC AAAGTAAATT CTTAACTTTG AATGGTAAAA AATATTACTT TGATAATAAC | nucleotides 82-144 of Seq. I.D. |

-continued

| | | | |
|---|---|---|---|
| | | TCA 3' | No. 1. |
| iii) | C | 5' GAAGCAGCTA CTGGATGGCA AACTATTGAT GGTAAAAAAT ATTACTTTAA TACTAACACT GCT 3' | nucleotides 208-270 of Seq. I.D. No. 1. |
| iv) | D | 5' ATAGCTTCAA CTGGTTATAC AATTATTAAT GGTAAACATT TTTATTTTAA TACTGATGGT ATT 3' | nucleotides 334-396 of Seq. I.D. No. 1. | v) DNA sequences consisting of sequences that are fully complementary to sequence A, B, C or D;
vi) DNA sequences that are partial subsequences of the DNA sequence A, B, C or D, such partial subsequences having a minimum of 15 consecutive nucleotide bases;
vii) DNA sequences that are partial subsequences of the DNA sequence that are fully complementary to sequence A, B, C or D, such partial subsequences having a minimum of 15 consecutive nucleotide bases;
viii) RNA sequences having a sequence as defined in sequence A, B, C, or D but with U replacing T; and
ix) RNA sequences having a partial subsequence A, B, C or D, the partial subsequence having a minimum of 15 consecutive nucleotide bases and with U replacing T in the partial sequence.

12. An oligonucleotide probe according to claim 11, wherein said probe is from 15 to 30 nucleotide bases in length.

13. An oligonucleotide probe according to claim 11, wherein said oligonucleotide sequence is a DNA sequence.

14. An oligonucleotide probe according to claim 11 wherein the label attached to the oligonucleotide sequence is selected from the group consisting of radioactive labels, fluorescent labels and enzyme labels.

15. An oligonucleotide probe according to claim 11, wherein said oligonucleotide sequence is immobilized onto a solid support.

16. An oligonucleotide probe for use in detecting DNA or RNA from microorganisms of the species *Clostridium difficile*, said probe consisting of an oligonucleotide sequence labelled with a label permitting detection of the probe when hybridized to a complementary sequence of *C. difficile* DNA or mRNA, said oligonucleotide sequence being selected from the group consisting of

| | | | |
|---|---|---|---|
| i) | A | 5' ATAGGGGTGT TTAAAGGACC TAAAGGATTT GAATATTTTG CACCTGCTAA TACTTATAAT AATAACATAG AAGGTCAGGC T 3' | nucleotides 1–81 of Seq. I.D. No 1 |
| ii) | C | 5' GAAGCAGCTA CTGGATGGCA AACTATTGAT GGTAAAAAAT ATTACTTTAA TACTAACACT GCT 3' | nucleotides 208–270 of Seq. I.D. No 1 | iii) DNA sequences consisting of sequences that are fully complementary to sequence A or C;
iv) DNA sequences that are partial subsequences of the DNA sequence A or C, such partial subsequences having a minimum of 15 consecutive nucleotide bases;
v) DNA sequences that are partial subsequences of the DNA sequences that are fully complementary to sequence A or C, such partial subsequences having a minimum of 15 consecutive nucleotide bases;
vi) RNA sequences having a sequence as defined in sequence A or C but with U replacing T; and
vii) RNA sequences having a partial subsequences of A or C, the partial subsequence having a minimum of 15 consecutive nucleotide bases and with U replacing T in the partial sequence.

17. An oligonucleotide probe according to claim 16, wherein said probe is from 15 to 30 nucleotide bases in length.

18. An oligonucleotide probe according to claim 17, wherein said oligonucleotide sequence is a DNA sequence.

19. An oligonucleotide probe according to claim 17 wherein the label attached to the oligonucleotide sequence is selected from the group consisting of radioactive labels, fluorescent labels and enzyme labels.

20. An oligonucleotide probe according to claim 17 wherein the oligonucleotide sequence is immobilized onto a solid support.

21. A method of detecting the presence of *C. difficile* DNA or mRNA in a sample which comprises treating the sample with an oligonucleotide probe as claimed in claim 28 and under conditions such that the probe can hybridize to the genetic DNA or mRNA so that a hybridization product is formed, and detecting the presence of said DNA or mRNA in the sample by detecting the presence of the hybridized labelled probe.

22. A method according to claim 21 wherein the oligonucleotide probe is from 15 to 30 nucleotide bases in length.

23. A method according to claim 22 wherein the oligonucleotide probe is a DNA probe.

24. A method of amplifying *C. difficile* DNA in a sample which comprises subjecting said DNA to a polymerase chain reaction using as primers a pair of oligonucleotides as claimed in claim 1, the oligonucleotide sequences used as primers being DNA sequences.

25. A method of amplifying *C. difficile* DNA in a sample which comprises subjecting said DNA to a polymerase chain reaction using as primers a pair of oligonucleotides as claimed in claim 3, the oligonucleotide sequences used as primers being DNA sequences.

26. A method according to claim 25 wherein the primers used are the oligonucleotides:

5' GAAGCAGCTA CTGGATGGCA 3' nucleotides 208–226 of Seq. I.D. No.1, 5' AGCAGTGTTA GTATTAAAGT 3' complementary of nucleotides 251–270 to Seq. I.D. No.1.

27. A method according to claim 25 wherein the primers used are the oligonucleotides:

5' ATAGGGGTGT TTAAAGGACC T 3' nucleotides 1–27 of Seq. I.D. No.1, 5' AGCCTGACCT TCTATGTTAT 3' complementary of nucleotides 62–81 to Seq. I.D. No.1.

28. A method according to claim 21 wherein the sample is a clinical sample.

29. A method according to claim 28 wherein the sample is a faecal sample.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
      ( A ) LENGTH: 1948 base pairs
      ( B ) TYPE: nucleic acid
      ( C ) STRANDEDNESS: double
      ( D ) TOPOLOGY: linear ( i i ) MOLECULE TYPE: DNA (genomic)

( v i ) ORIGINAL SOURCE:
      ( A ) ORGANISM: Clostridium difficile ( x i ) SEQUENCE DESCRIPTION: SEQ ID NO: 1:

ATAGGGGTGT TTAAAGGACC TAAAGGATTT GAATATTTTG CACCTGCTAA TACTTATAAT 60

AATAACATAG AAGGTCAGGC TATAGTTTAT CAAAGTAAAT TCTTAACTTT GAATGGTAAA 120

AAATATTACT TTGATAATAA CTCAAAAGCA GTTACCGGAT GGCAAACTAT TGATAGTAAA 180

AAATATTACT TTAATACTAA CACTGCTGAA GCAGCTACTG GATGGCAAAC TATTGATGGT 240

AAAAAATATT ACTTTAATAC TAACACTGCT GAAGCAGCTA CTGGATGGCA AACTATTGAT 300

GGTAAAAAAT ATTACTTTAA TACTAACACT GCTATAGCTT CAACTGGTTA TACAATTATT 360

AATGGTAAAC ATTTTTATTT TAATACTGAT GGTATTATGC AGATAGGAGT GTTTAAAGGA 420

CCTAATGGAT TTGAATATTT TGCACCTGCT AATACGGATG CTAACAACAT AGAAGGTCAA 480

GCTATACTTT ACCAAAGTGA ATTCTTAACT TTGAATGGTA AAAAATATTA TTTTGATAAT 540

AACTCAAAAG CAGTTACCGG ATGGCAAACT ATTGATAGTA AAAAATATTA CTTTAATACT 600

AACACTGCTA TAGCTTCAAC TGGTTATACT ATTATTAATG GAAAACATTT TTATTTAAAT 660

ACTGATGGTA TTATAGCTTC AACTGGTTAT ACAATTATTA ATGGTAACCA TTTTTATTTT 720

AATACTGATG GTATTATGAA AATAGGGGTT TTTAAAGGAC CTAATGGATT TGAATATTTT 780

GCACCTGCTA ATACTGATCA TAATAATATA GAAGGTCAGG CTATAGTTTA TCAAAGTAAA 840

TTCTTAACTT TGAATGGTAA AAAATATTAT TTTGATAATA ATTCAAAAGC AGTTACTGGA 900

TGGCAAACTA TTGATAGTAA AAAATATTAC TTTAATACTA ACACTGCTGA AGCAGCTACT 960

GGATGGCAAA CTATTGATGG TAAAAAATAT TACTTTAATA CTAACACTGC TGAAGCAGCT 1020

ACTGGATGGC AAACTATTGA TGGTAAAAAA TATTACTTTA ATACTAACAC TGCTATAGCT 1080

TCAACTGGTT ATACAATTAT TAATGGTAAA CATTTTTATT TTAATACTGA TGGTATTATC 1140

GGAGTGTTTA AAGGACCTAA TGGATTTGAA TATTTTGCAC CTGCTAATAC TGATGCTAAT 1200

AACATAGAAG GTCAAGCTAT AGTTTATCAA AGTAAATTTT TAACTTTGAA TGGTAAAAAA 1260

TATTACTTTG ATAATAACTC AAAAGCAGTT ACTGGATGGC ATACTATTGA TAGTAAAAAA 1320

TATTACTTTA ATACTAACAC TGCTGAAGCA GCTACTGGAT GGCAAACTAT TGATGGTAAA 1380

AAATATTACT TTAATACTAA CACTGCTATA GCTTCAACTG GTTATACAAT TAATAATGGA 1440

AAACATTTTT ATTTTAATAC TGATGGTATT ATAGGAGTGT TTAAAGGACC TAATGGATTT 1500

GAATATTTTG CACCTGCTAA TACGGATGCT AACAACATAG AAGGTCAAGC TATAGTTTAT 1560

CAAAGTAAAT TCTTAACTTT GAATGGTAAA AAATATTATT TTGATAATAA CTCAAATGCT 1620

GTTACCGGAT GTCAAACTAT TGATAGTAAA AAATATTACT TTAATACTAA CACTGCTATA 1680

```
GCTTCAACTG GTTATACAAT TATTAATGGT AAACATTTTT ATTTTAATAC TGATGGTATT   1740

ATAGGGGTGT TTAAAGGTCC TAATGGATTT GAATATTTTG CACCTGCTAA TACTTATGAT   1800

AATAACATAG AAGGTCAGGC TATAGTTTAT CAAAGTAAAT TATTAACTTT GAATGGTAAA   1860

AAATATTATT TTGATAATAA CTCAAAAGCA GTTACCGGAT GGCAAACTAT TGATAGTAAA   1920

AAATATTACT TTAATACTAA CACTGCAG                                      1948
```

( 2 ) INFORMATION FOR SEQ ID NO: 2:

( i ) SEQUENCE CHARACTERISTICS:
    ( A ) LENGTH: 1853 base pairs
    ( B ) TYPE: nucleic acid
    ( C ) STRANDEDNESS: double
    ( D ) TOPOLOGY: linear   ( i i ) MOLECULE TYPE: DNA (genomic)

( v i ) ORIGINAL SOURCE:
    ( A ) ORGANISM: Clostridium difficile   ( x i ) SEQUENCE DESCRIPTION: SEQ ID NO: 2:

```
AAAATAGTAA AAAAGTAGTG ATAGCTGCTG TAAACGGATT TGCTTTAGGT GGATGTGAAC     60

TTGCAATGGC ATGTGATATA AGAATTGCAT CTGCTAAAGC TAAATTTGGT CAGCCAGAAG    120

TAACTCTTGG AATAACTCCA GGATATGGAG GAACTCAAAG GCTTACAAGA TTGGTTGGAA    180

TGGCAAAAGC AAAACAATTA ATCTTTACAG GTCAAGTTAT AAAAGCTGAT GAAGCTGAAA    240

AAATAGGGCT AGTAAATAGA GTCGTTGAGC CAGACATTTT AATAGAAGAA GTTGAGAAAT    300

TAGCTAAGAT AATAGCTAAA AATGCTCAGC TTGCAGTTAC ATACTCTAAA GAAGCAATAC    360

ACTTGGTGCT CAAACTGATA TAAATACTGG AATAGATATA GAATCTAATT TATTTGGTCT    420

TTGTTTTTCA ACTAAACACC AAAAGAAGG AATGTCAGCT TTCGTTGAAA AGAGAGAAGC     480

TAAGTTTATA AAAGGGTAAA AATCTAATTA AAAATATATT TGCTGTTAAC TAGAATAATT    540

TAAATAGTAT TTTAATCTAG TTAACATAAT ATAAATACTA AATAACAGG AGGTTATAAC     600

TATGAAATTA GCTGTAATAG GTAGTGGAAC TATGGGAAGT GGTATTGTAC AAACTTTTGC    660

AAGTTGTGGA CATGATGTAT GTTTAAAGAG TAGAACTCAA GGTGCTATAG ATAAATGTTT    720

AGCTTTATTA GATAAAAATT TAACTAAGTT AGTTACTAAG GGAAAATGGA TGAAAGCTAC    780

AAAAGCAGAA ATATTAAGTC ATGTTAGTTC AACTACTAAC TATGAAGATT TAAAAGATAT    840

GGATTTAATA ATAGAAGCAT CTGTAGAAGA CATGAATATA AAGAAAGATG TTTTCAACTT    900

ACTAGATGAA TTATGTAAAG AAGATACTAT CTTGGCAACA AATACTTCAT CATTATCTAT    960

AACAGAAATA GCTTCTTCTA CTAAGAGACC AGATAAAGTT ATAGGAATGC ATTTCTTTAA   1020

TCCAGTTCCT ATGATGAAAT TAGTTGAAGT TATAAGTGGT CAGTTAACAT CAAAAGTTAC   1080

TTTTGATACA GTATTTGAAT TACTTAAGAG TATCAATAAA GTACCAGTAG ATGTATCTGA   1140

ATCTCCTGGA TTTGTAGTAA ATAGAATACT TATACCTATG ATAAATGAAG CTGTTGGTAT   1200

ATATGCAGAT GGTGTTGCAA GTAAAGAAGA AATAGATGAA GCTATGAAAT TAGGAGCAAA   1260

CCATCAATGG ACCACTAGCA TTAGGTGATT TAATTGGATT AGATGTTGTT TTAGCTATAA   1320

TGAACGTTTT ATATACTGAG TTTGGAGATA CTAAATATAG ACCTCATCAC TTTTAGCTAA   1380

AATGGTTAGA GCTAAGCAAT TAGGAAGAAA AACTAAGATA GGATTCTATG ATTATAATAA   1440

ATAAGAATTT GGAATAAAAG TTTAAATAAA ATTGTTTAAA AACAATTTCG ATATATGAAA   1500

AAATCTAATT TAATGGGGGT AATGATATGA GAGAAGTAGT AATTGCCAGT GCAGCTAGAA   1560

CAGCAGTAGG AAGTTTTGGA GGAGCATTTA AATCAGTTTC AGCGGTAGAG TTAGGGGTAA   1620
```

-continued

```
CAGCAGCTAA AGAAGCTATA AAAAGAGCTA ACATAACTCC AGATATGATA GATGAATCTC 1680

TTTTTAGGGG GAGTACTTAC AGCAGGTCTT GGACAAAATA TATAGCAAGA CAAATAGCAT 1740

TAGGAGCAGG AATACCAGTA GAAAAACCAG CTATGACTAT AAATATACTT TGTGGTTCTG 1800

GATTAAGATC GTGGCGGGCA CTCCGAACGT GAACGGGTCC GCGTCGACCT GCA        1853
```